United States Patent [19]

Roos et al.

[11] Patent Number: 4,697,075
[45] Date of Patent: Sep. 29, 1987

[54] X-RAY IMAGING SYSTEM CALIBRATION USING PROJECTION MEANS

[75] Inventors: Hartog J. Roos, Brookfield; Edward F. Schilling, West Allis, both of Wis.

[73] Assignee: General Electric Company, Milwaukee, Wis.

[21] Appl. No.: 850,515

[22] Filed: Apr. 11, 1986

[51] Int. Cl.⁴ .............................................. H01J 31/50
[52] U.S. Cl. ............................... 250/213 VT; 378/207
[58] Field of Search ................. 250/213 VT; 358/139, 358/111, 101, 231; 378/207, 206; 353/30, 65

[56] References Cited

U.S. PATENT DOCUMENTS 3,558,893  1/1971  Ball ............................. 250/213 VT
4,511,927  4/1985  Bauer ................................. 358/231

Primary Examiner—David C. Nelms
Assistant Examiner—Chung Seo
Attorney, Agent, or Firm—James H. Beusse; Douglas E. Stoner

[57] ABSTRACT

An image evaluation apparatus for quantitative and qualitative evaluation of an optical image generated by an x-ray imaging system of the type including an x-ray source, an image intensifier tube for converting received x-ray radiation to optical images to be recorded photographically and/or electronically. The evaluation apparatus comprises an image projection device in the form of a cylindrical housing having a lens mounted in one end and a light diffuser mounted in a second end. The lens is of the type having a focal point at infinity such that all of the light passing through the lens is substantially parallel. The evaluation apparatus is mounted to the x-ray imaging system in a position normally occupied by one of the recording or display apparatus so as to be in a position for receiving light generated by the optical image on the image intensifier tube. The received light is focused onto the diffuser and its intensity is measured using a light photometer. The intensity distribution measurement on the diffuser provides an indication of the performance of the imaging system including the intensifier tube and associated optical transmission elements in the light transmission path.

10 Claims, 5 Drawing Figures

X-RAY IMAGING SYSTEM CALIBRATION USING PROJECTION MEANS

BACKGROUND OF THE INVENTION

The present invention relates to x-ray apparatus and, more particularly, to a method and apparatus for in situ evaluation of imaging apparatus in an x-ray system.

In x-ray apparatus, x-ray radiation responsive apparatus is positioned in a line with an object and an x-ray source whereby x-rays from the source pass through and are attenuated by the object before impinging on the x-ray sensitive apparatus to thereby obtain an image of the object. One type of x-ray apparatus is a "spot film" system which includes a table on which an object, e.g., a patient, is positioned and a motor driven mechanism within the table for moving the table to various desired locations. An imaging apparatus is positioned above the patient and also includes mechanisms for moving the imaging apparatus into selected positions with respect to the patient. The imaging apparatus may include a film holding mechanism for positioning sheets of x-ray film in desired locations or may include a mechanism for positioning an x-ray sensitive electronic device in position for sensing the x-rays coming through the object. The electronic device may comprise an image intensifier tube which responds to the x-ray radiation by generating an optical image having an optical intensity proportional to the intensity of the received x-rays.

In the system utilizing the electronic imaging apparatus, the optical image generated by the apparatus may be transmitted to a plurality of recording or readout devices. A recording device may include a cine film camera and video tape recorder. A read-out device may comprise simply a television camera positioned to sense the optical image and to transmit the image to a television display.

In order to present the fluoroscopic image, i.e., the optical image of the x-ray attenuation effects in an object, in a suitable form for display on the television monitor, numerous energy conversions occur. First, the electronic sensor such as, for example, the image intensifier tube, converts the incident x-ray information to a visible light image of increased brightness. An optical system, usually consisting of two very fast, highly corrected lenses, projects this image onto the pick-up tube in the television camera. This image is then converted into a television signal, transmitted over a connecting cable, and displayed on the monitor for observation. When film cameras are added into the system, more complex optical systems are required. Film cameras may include cine cameras for high speed recording of dynamic phenomena and seventy to one hundred or more millimeter cameras for use as supplementary spot film cameras.

Because of the numerous energy conversions occurring in the x-ray to optical image system, and because of the complex optics involved in transmitting the images, the imaging system becomes very susceptible to alignment variations, light attenuation or losses in optics and to variations in the quality of the image generated by the image intensifier tube.

In present day systems, once the x-ray apparatus has been placed into use, it becomes very difficult for the user to determine whether deterioration in picture or image quality is due to a failure or deterioration of components of the system and which if any of the components have deterioated. Quite often, misalignment or loss of alignment of various optical components in the system may result in deterioration of image quality. The primary suspect component in most image quality problems is the image intensifier tube. In general, due to the cost of the x-ray apparatus and the need to have the apparatus available at all times, the user will often elect to replace the image intensifier tube whenever image quality deteriorates. Quite often, tube replacement does not solve the image problem. Nevertheless, the cost and time involved in changing the tube must be incurred in order to determine whether or not the tube is the deteriorated variable. Such cost in a typical x-ray spot film apparatus is relatively high and may require an average of sixteen hours to change a tube and realign the system with a new tube in place. If such change out does not resolve the deterioration problem, further changes in the system may be required. Accordingly, it would be advantageous to provide a method and apparatus to enble quantitative and qualitative evaluation of an x-ray imaging apparatus without the necessity of a major overhaul.

In x-ray imaging apparatus utilizing both high speed cine film recording and television monitor displays, the image generated by the image intensifier tube is split between the two display and recording apparatus. The splitting of the image is accomplished by use of a beam splitter, i.e., a semi-transparent mirror which allows part of the light to pass through the mirrored surface while reflecting a portion of it towards one of the recording or display devices. In some applications, a third device such as a magnetic recording apparatus may also be utilized and in those cases the beam splitter may have to be switched between various selected positions in order to accommodate recording on the selected devices. Because of the movement of the beam splitter, it is possible that the beam splitting mirror may not return to exactly a desired location and may result in an image not being precisely positioned on one of the recording or display devices. If this were to happen, the image quality would deteriorate and the user would be unable to determine whether the deterioration was due to the beam splitter or to the image intensifier tube.

Still further, the optics in the imaging system are highly corrected lenses arranged in an infinite conjugate system. This arrangement means that light entering the lens from one of the conjugate points associated with the lens has all the rays from a single point of the target essentially parallel. In other words, in the case of an image intensifier, the output screen of the image tube is located at the focal point of the objective lens so that all the rays originating from any one point of the phosphor on the output screen emerge parallel from the lens. It will be appreciated that the lensing system includes a plurality of individual lenses precisely located with respect to each other. Any shifting of the lensing system will result in the deterioration of image quality. Furthermore, it is not unusual for the lensing system to have particular areas around the periphery such that light rays passing through the periphery are not precisely parallel and thus operate to diffuse the image and to further deteriorate image quality. For this reason, it is important to position the lensing system such that the light rays pass through that portion which provides the best image quality. However, as with the beam splitter, once the system has been set up and is being used, it becomes difficult if not impossible to determine from the generated image whether the system deterioration is caused by the image intensifier tube, the optical system or the beam splitter. Since the optical lens system and beam splitter may be aligned to correct any image deterioration, it would be advantageous to provide a method and apparatus for quantitative and qualitative evaluation of these components of an x-ray system without the necessity of having to disassemble the system and change components to determine which component is creating the image deterioration.

SUMMARY OF THE INVENTION

The above and other desirable objects are achieved in an x-ray imaging system by utilization of a method and apparatus for quantitatively and qualitatively evaluating the image system without disassembling any components of the system. In an illustrative embodiment, image evaluation apparatus is disclosed for use in an x-ray imaging system including an electronic imaging device such as an image intensifier, tube mounted for receiving x-ray radiation and for converting the x-ray radiation to an optical image. The imaging system includes optics for transmitting the optical image to a plurality of image recording and sensing devices such as, for example, a cine camera, a television camera with or without a magnetic recording system and associated monitoring set. Each of the image recording and presentation devices is positioned so as to record and monitor the optical image provided by the image intensifier tube. In utilizing the invention, one of the devices is removed and replaced by the image evaluation apparatus which comprises an elongated housing having one end adapted to connect to the position at which the imaging device it replaced was removed. A second end of the housing includes a mounting arrangement for receiving a light diffuser. A lens is mounted in the housing adjacent the end connected to the x-ray imaging system for focussing the optical image generated by the image intensifier tube on the diffuser. The lensing system is focused at infinity such that the light rays passing through the lensing system are essential parallel. The diffuser allows the intensity of the light passing through the lens to be monitored on its surface at selected points for determining the light distribution generated by the image intensifier tube. To this end, a light intensity measuring apparatus for measuring light intensity at selected spots on the light diffuser is provided. In order to minimize any extraneous effects due to external light sources, the light diffuser is covered by a light impervious panel having holes formed therein for receiving the light intensity measuring device.

In practicing the method of the invention, in one form, the image evaluation apparatus is placed on the imaging system aligned along the optical axis of the image intensifier tube. Any beam splitter located in the imaging system is moved out of the field of view to preclude any effects of the beam splitter. By then evaluating the light distribution across the light diffuser, the quality of the image generated by the image intensifier tube can be determined. The optical lensing system within the imaging system can be evaluated by stopping down the aperture located above the lens and quantifying the light distribution across the image. By determining the uniformity of the intensity across the image, a defective imaging system can be determined. Furthermore, by providing a light diffuser having centering rings, the objective lens in the imaging system can be positioned to allow the image to be centered and aligned. The beam splitter can be similarly evaluated by measuring the intensity of the light passing through the beam splitter.

In another embodiment of the invention, the image evaluation apparatus can be utilized in conjunction with a calibrated light source for verifying the operation of the image recording and presentation devices connected to the imaging system. By replacing the diffuser with a reticle pattern and attaching a uniform light source of predetermined level, the imaging apparatus when adopted with its lens side to a recording camera can be used to align and evaluate recording camera performance.

DESCRIPTION OF THE DRAWING

For a better understanding of the present invention, reference may be had to the following detailed description taken in conjunction with the accompanying drawing in which:

FIG. 4 is a simplified functional cross sectional diagram illustrating use of the present invention.

DETAILED DESCRIPTION

Figure 1:
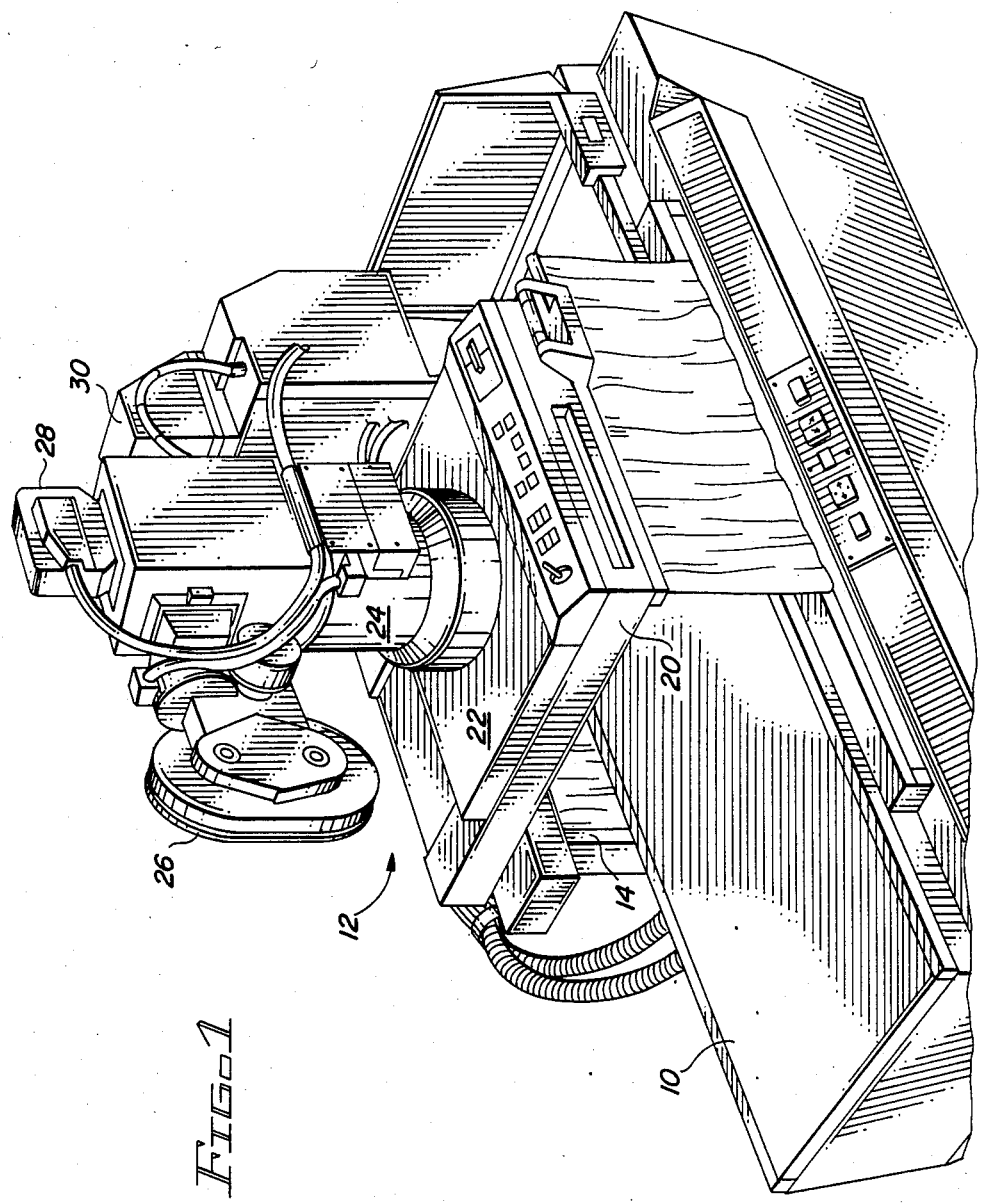
FIG. 1 is a simplified perspective view of an x-ray spot film apparatus with which the present invention is useful.

Referring now to FIG. 1, there is shown a simplified perspective view of an x-ray spot filming apparatus with which the present invention is particularly useful. The apparatus includes an x-ray table 10 and a spot filming apparatus 12. The spot filming apparatus 12 is supported above the table 10 on a column 14. The apparatus 12 can be moved vertically to raise or lower a film or an image responsive device with respect to the upper surface of the table 10. The table 10 is supported by a pedestal 16. The table surface 10 may be moved either laterally or longitudinally with respect to the spot film apparatus 12. The top of the table 10 constitutes a planar patient examining surface.

The spot filming apparatus 12 and the support tower 14 are also capable of movement transversely with respect to the table top 10 by means of a support carriage (not shown). A conventional x-ray tube or source (not shown) attached to the support carriage is located within the table support table 16.

The spot filming apparatus 12 is attached to the tower 14 by a support frame that includes a pair of transversely extending arms on which the spot filming apparatus 12 slides. The support arms are attached to the tower 14 for vertical movement in order to position the spot filming apparatus 12 with respect to a patient located on the table 10. Side support rails 20 support the spot filming apparatus for transverse movement with respect to the table 10. The spot filming apparatus 12 is manually moved between a rearward position and a forward position (the position shown in FIG. 1). In the rear position, the apparatus 12 is out of the direct line of the x-ray source radiation and is located in what is referred to as a non-operating position. In the forward or operating position, the spot filming apparatus 12 overhangs the patient examining surface on top of table 10.

The spot filming apparatus 12 comprises a number of independent elements. The planar portion located adjacent the side rails 20 contains the apparatus for positioning x-ray film at predetermined locations for obtaining film images of a patient located on the table 10. The film located within the portion 22 can be moved to different positions by motors positioned within the portion 22 which drive the film to desired locations. In at least one location, the film is moved out of the line of x-ray radiation so the x-ray radiation may pass through the portion 22 and enter into an electronic x-ray responsive image development apparatus 24. Preferably the apparatus 24 includes an image intensifier tube of a type well known in the art. Within the apparatus 24 there is located imaging optics and beam splitters for directing the image generated by the image intensifier tube to selected recording and presentation instruments. In FIG. 1, one of the recording instruments is indicated at 26 as a cine camera for obtaining high speed photographic images of selected portions of a patient's anatomy. Electronic recording of images generated by the apparatus 24 is obtained by a TV camera 28 in conjunction with a magnetic recorder positioned at the upper end of the apparatus 24. Since it is also desirable for an operator to be able to continuously view the x-ray image being created, one or more television monitors are used with a TV camera 30 and recorder.

Figure 2:
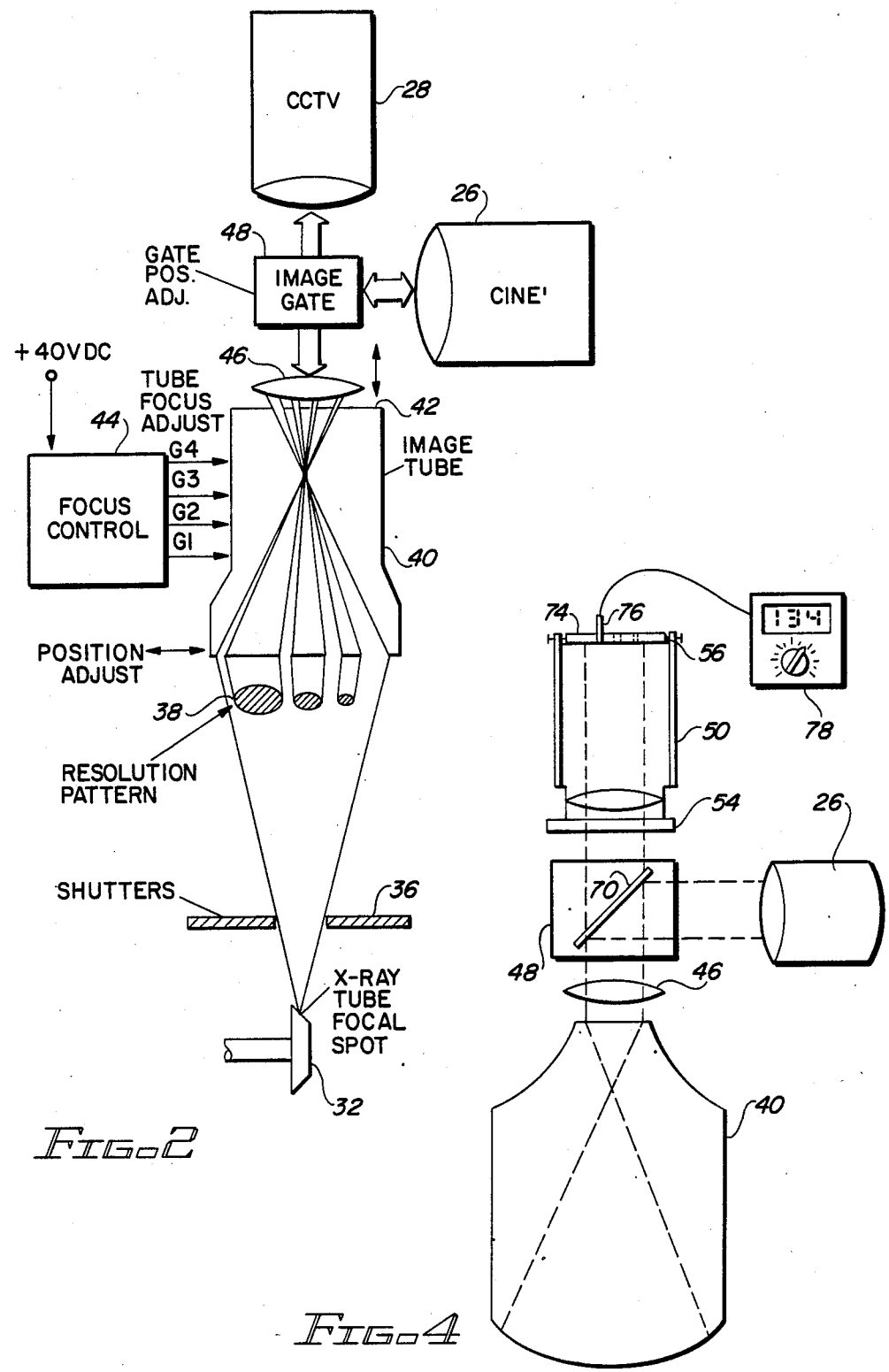
FIG. 2 is a functional diagram of the x-ray imaging portion of the apparatus of FIG. 1.

In some application, through the use of a movable beam splitter, the functions of camera 28 and cameras 26 and 30 are combined. Referring now to FIG. 2, there is shown a functional diagram of the x-ray imaging portion of the apparatus illustrated in FIG. 1. The x-ray source is indicated at 32 for generating x-ray radiation 34 which passes through a collimator and shutter arrangement 36 to generate a directed beam of radiation onto a object positioned at the surface of table 10. For purposes of illustration, the object is shown in FIG. 2 as a resolution pattern 38. The resolution pattern 38 is a sequence of elements which provide varying degrees of radiation absorption and also provide a pattern for presentation in order to determine the resolution of the system. The x-ray radiation beam 34 impinges on a phosphor face of an image intensifier tube 40 which converts the x-ray radiation to an optical image at a second or output face 42. A focus control 44 controls various grid elements in the imaging tube 40 so that the image can be appropriately focused at the surface 42.

The optical image generated at surface 42 is projected through an objective lens 46 to an image gate 48. The image gate 48 includes a beam splitter (not shown) and appropriate electromechanical positioning apparatus for positioning the beam splitter so as to direct the optical image to both the TV camera 28, the cine camera 26 and photospot camera 30. All the cameras 26, 30 and 28 include camera lenses which collect the light emanating from the objective lens 46 and form an image of the output screen 42 on the pick-up tube within the cameras 28 and 30 or on the film located within the camera 26. It should be noted here that the objective lens 46 and the lens of a corresponding camera operate together to form an infinite conjugate system. The conjugate ratio in an imaging system is the ratio of the expected subject distance as compared to the expected image distance. In the x-ray imaging system, one of the conjugates is considered to be at infinity such that light entering the lens from this infinite conjugate has all the rays from a single point of the subject essentially parallel. By definition, the other conjugate, that of the image distance, must be equal to the focal length of the lens. While lenses designed to have one conjugate infinitely long will work at other object image distances, their maximum resolution is realized when they are used at the conjugates for which they were designed. If one of the lenses is to be used as a collimating lens, which means that the infinitely long conjugate is in image space, then the object for this lens must be at the focal point of the lens. Compared to the way such a lens would work in a standard camera, it is arranged in a reverse situation in an x-ray imaging system. In other words, the output screen 42 of the tube 40 is located at the focal point of the objective lens so that all of the rays originating from any one point of the phosphor on the output screen emerge parallel from the lens. It will be appreciated that the lens 46 comprises a plurality of individual elements and may have as many as seven to nine individual glass elements in order to achieve the very high correction of aberration. Such an arrangement would require forty different variables be considered in the design of the lens, including for example, the radius of curvature of each surface of each of the nine elements plus the air space between the elements, the index of refraction of each element and the disbursive power of each element.

In addition to the objective lens 46, the camera lens must also operate to collect the light emanating from the objective lens 46 and form an image of the output screen on either a pick-up tube in the camera 28 or on a film in the camera 26. For the camera lens, the infinite distance conjugate of the lens is on the object side. The image will therefor be formed at the focal plane of the camera lens. In operating in conjunction with the objective lens 46, the combination of camera lens and objective lens causes light originating from a source at the focal plane of the objective lens to be projected as a family of parallel beams into the camera lens which then forms an image of the source at its focal plane. Accordingly, it will be appreciated that the alignment of the objective lens 46 and the positioning of any fixed lens in the cameras 26 and 28 become very critical in obtaining high resolution x-ray images. Furthermore, any deterioration of the image at the output screen 42 becomes extremely difficult to diagnose as either a lens problem or a problem with the image tube 40.

For a more detailed description of an image intensifier tube such as that illustrated at 40, and to an associated control system for controlling the operation of the image tube 40 and the image gate 48, reference may be had to U.S. Pat. No. 3,491,239 issued Jan. 20, 1970 and assigned to General Electric Company.

Figure 3:
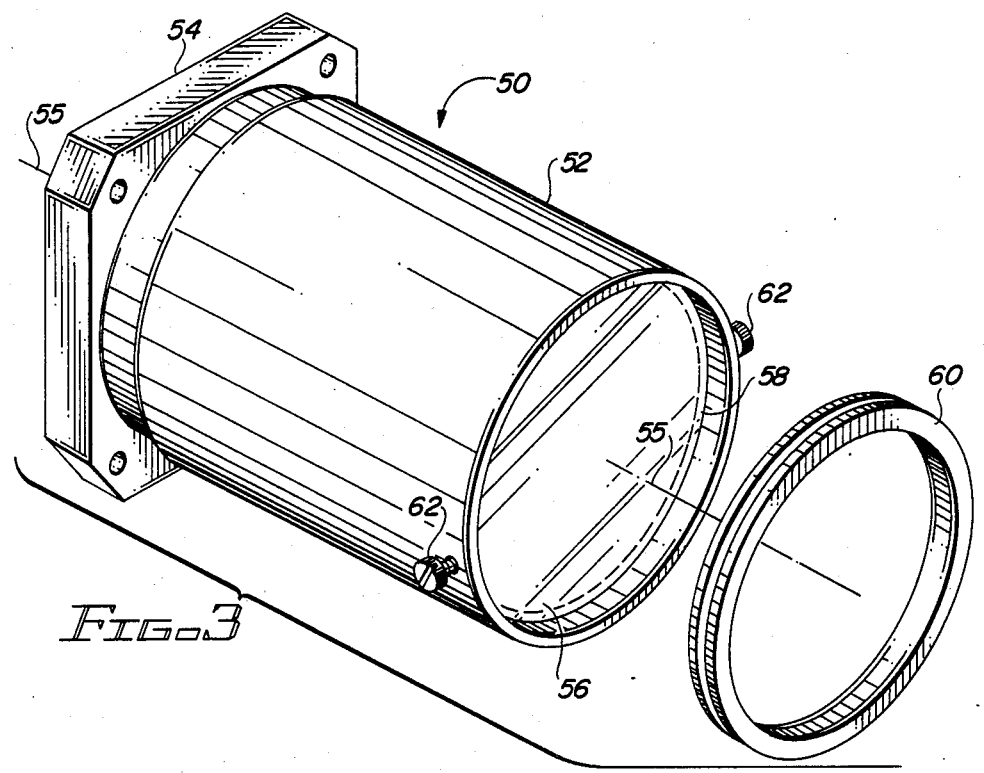
FIG. 3 is a perspective view of one embodiment of the present inventive image evaluation apparatus.

Referring now to FIG. 3, there is shown a perspective view of an image evaluation apparatus for in situ quantitative and qualitative evaluation of the imaging apparatus 12 of FIG. 1. The tool indicated generally at 50 comprises a generally cylindrical elongated housing 52 having one end attached to a substantially flat mounting base plate 54. A longitudinal axis 55 of housing 52 is normal to the plane of the mounting surface of the plate 54. A second end of the housing 52 has a slightly enlarged opening which has been machined to form an internal shoulder or shelf on which a light diffuser 56 may be positioned. The internal shoulder is indicated by the dashed lines 58. Once the light diffuser has been positioned within the housing 52, a retaining ring 60 is placed over the diffuser 56 and held in place by thumb screws 62 passing through threaded apertures in housing 52. The retaining ring 60 has a circular groove 64 about its outer periphery. The thumb screws 60 when tightened will extend into the groove so as to hold the ring firmly in position against the light diffuser 56. The mounting plate 54 is machined to fit precisely square against the mounting bracket to which each of the image recording devices such as the cameras 26, 28 and 30 are normally attached. In this manner, the image which would normally be presented to the cameras is focused through the apparatus 50 and appears on the light diffuser 56. The focusing of the image onto the diffuser 56 is accomplished by an objective lens or set of lenses 72 (see FIG. 4) located in the apparatus 50 adjacent the mounting plate 54. The lenses are designed to provide for the transmittal of light from the objective lens 46 in a path which is essentially parallel from any point in the image so that the light at the diffuser 56 is not focused to a specific point as would occur with a standard camera lens. In other words, the lens 72 has a focal point of infinity.

Turning now to FIG. 4, there is shown a cross sectional view of a portion of the imaging apparatus 12 and the image evaluation apparatus 50 in an operative arrangement. The image generated by the image tube 40 is focused by the objective lens 46 through the image gate 48. Within the image gate 48 is a beam splitter 70 which divides the light emanating from lens 46 into one portion which is transmitted to the camera 26 and a second portion which is transmitted to the image evaluation apparatus 50. As will be apparent from further discussions regarding the method of using the image evaluation tool, it will be apparent that in some applications the beam splitter 70 is moved completely out of the beam such that all of the light emanating from the lens 46 passes to the apparatus 50. Within the apparatus 50, the light is transmitted through its lens 72 which assures that the light rays are focussed on the diffuser 56. The design of objective lenses such as 72 for parallel light transmission is well known to those skilled in the art. A light impervious plate 74 is positioned over the light diffuser 56 to block external light and prevent such light from affecting the validity of light intensity readings taken across the diffuser 56. The plate 74 has a plurality of apertures formed therethrough for allowing a light sensor 76 to be placed in position to read light at a specific spot on the diffuser 56. The signals generated by the light sensor 76 are provided to a meter 78 which provides a read out of the light intensity on the monitored spot on the diffuser 56. By moving the sensor 76 to the different apertures formed through the plate 74, a sequence of light intensity values can be taken at various selected areas on the diffuser 56. Typically, such areas might include the fringe areas around the periphery of the image and a central reading at the center of the plate 56.

The system arrangement illustrated in FIG. 4 allows image system parameters such as conversion factor, contrast ratio and light output uniformity to be quantitatively measured through the image transmission path of apparatus 12. Furthermore, the image evaluation apparatus 50 in the arrangement illustrated can also be used as an alignment tool for the entire image system including the optics and image gate 48. In order to achieve these desirable results of alignment and evaluation of quantitative factors, the light diffuser 56 may be constructed in various alternative forms. For light intensity measurements, the diffuser 56 may be a simple light diffusing plate. For other types of measurement, the light diffuser may have various types of graticles inscribed on the plate to enable precise measurement of image size and position. A complete set of graticles for evaluating all of the components of the imaging system would require several different patterns.

The plate 74 acts as a guide plate and a support for the spot photometer light sensor 76. It provides repeatability of sensor placement with respect to a projected image. While a two hole plate 4 may be utilized and thus only two measurements required for contrast ratio measurement, the plate 74 requires at least six holes for uniformity measurement and measurement of cardiovascular phantom images. The four middle holes structured around a center hole are located proportional to 50% radius of the image to be measured. The outer hole is located proportional to the edge of the image to be measured.

One of the graticles mentioned above is for use as light diffuser 56, six of the graticles are specifically designed for alignment of the television camera and equipment and two for image tube sizing and gate alignment. In the mode of operation in which the TV camera and tool are aligned, the image evaluation apparatus 50 is utilized as a light source rather than as illustrated in FIG. 4. When utilized as a light source, the plate 74 is replaced with a flat plate electroluminescent lamp 78 (shown in FIG. 5) whose intensity can be precisely controlled. The TV camera 28 or 30 is then connected to the mounting plate 54 to that the image projected to the camera is that image appearing on the graticle or light diffuser 56. One of the graticles may be, for example, a multiburst graticle with incremental sets of television resolution measurement lines from side to side. Such television patterns are well known in the TV art. Other forms of graticles for use in aligning cameras may include a resolution burst, with incremental sets of television resolution measurement lines with the highest resolution in the center, a cross-hatch pattern, a ten step linear grey scale, a star and resolution wedge pattern and a beam alignment pattern. While these particular patterns are not unique to this invention, the preparation of such patterns on a graticle for displaying the patterns to a television camera for camera alignment purposes using the present invention is considered to be a novel application.

In addition to the graticles mentioned above, three further graticles are also utilized in aligning the imaging system. Two of the graticles include sizing rings and diffuser for adjusting the system optics for precise image size and a standard flat field low density light diffusing plate for evaluating the operation of the intensifier tube 40.

Figure 5:
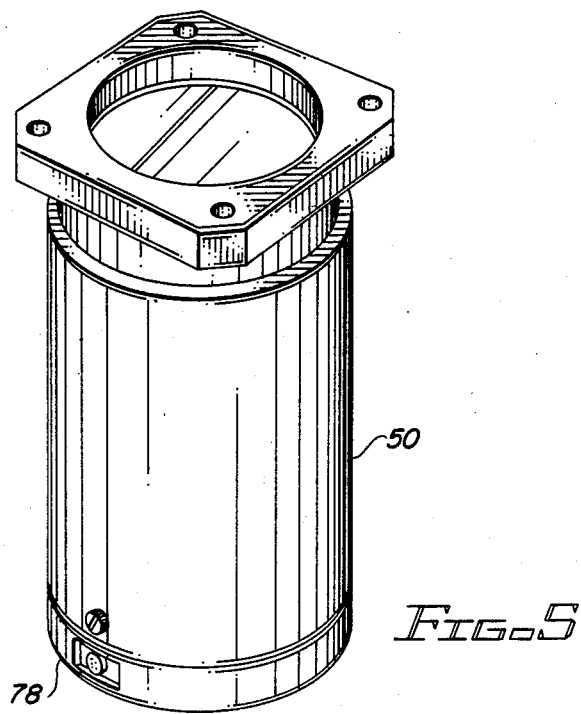
FIG. 5 is a planar view of the present inventive apparatus adapted for evaluating recording apparatus performance.

The detachable electroluminescent light source is shown attached to the image evaluation apparatus 50 in FIG. 5. The light source 78 provides a uniform light of approximately 540 nanometers with a maximum intensity of 40 foot/Lamberts when operated from a 970 Hz voltage source.

When the image evaluation apparatus 50 is attached to the imaging system 12 as shown in FIG. 4, the tool may be used to focus, size, center, align the gate 48 and measure the light output of the image system or image intensifier 40. When the tool 50 is connected to operate as an image transmitter as is shown in FIG. 5, it may be used to align, set up and evaluate a TV camera system and to align and focus photographic cameras.

In the operation of the image evaluation apparatus 50, the graticles or light diffusing plates 56 are precision optical devices which must be accurately positioned in the focal plane of the tool. The graticles in a preferred embodiment are chromium deposited on one side of a glass base. However, the grey scale graticle is an emulsion pattern sealed between two glass plates.

Because the image evaluation apparatus 50 is precisely designed to provide proper focusing and resolution of images generated by the image intensifier tube when mounted in the position of a recording instrument such as the camera 28, the adjustment of an image displayed on the apparatus 50 at the diffuser 56 is performed as a standard alignment of the imaging system 12. For example, the focus of the image generated by the tube 40 is achieved by appropriate adjustment of the focus control 44 which varies the voltages on the various grid elements in the tube 40. Sizing of the image generated by the image tube 40 is determined by placing a sizing graticle in the position of the diffuser 56 and adjusting the appropriate grid voltages on the tube 40. Optical focus is achieved by adjusting the position of the objective lens 46.

If it is desired to perform image gate 48 and beam splitter 70 alignment or performance evaluation, the image evaluation apparatus 50 is normally placed in the position of the cine camera 26. The intensity of the light reflected from the beam splitter 70 can then be measured by utilizing diffuser 56 with an appropriate guide plate 74 installed to allow measurement of light intensity at predetermined positions on the diffuser 56. The light meter sensor 76 provides a measurement of light intensity. If a prior measurement of system performance has been done by placing the image evaluation apparatus 50 along an axial direction of light travel as shown in FIG. 4, then any non-uniformities generated at the non-axial port such as that held by the camera 26, will indicate a problem or defect in the beam splitter 70, and replacement of the gate 48 or splitter 70 may be required.

The image evaluation apparatus 50 also provides a means for measuring the uniformity of the field generated by the x-ray system. Field uniformity may be affected by x-ray tube problems, lack of uniformity in the beam splitter 70, vignetting caused by the optics 46 and non-uniformities of the image tube 40. By placing the image evaluation tool 50 on an axial port without the beam splitter 70 in the field of view, the image tube 40, optics 46 and x-ray source 32 may be evaluated. In order to correlate the relative light output of the image tube 40, a cardiovascular phantom of a type well known in the art is placed in position on the table 10 and exposed to x-rays which are detected by image tube 40. The relative light output corresponding to the different cardiovascular phantom areas as measured with the apparatus 50 can be plotted on a sensitometric curve of a film taken from the cardiovascular phantom, on which the cardiovascular phantom densities have been plotted, providing correlation between system and film performance. This correlation information can be stored and retrieved for reference at a later time when the system is again evaluated.

A test of contrast ratio of the system can be performed by performing initial measurements on an operating imaging system and comparing those measurements to published image tube data and by comparing those measurements to the same system at a later time when performance has degraded. Similarly, the conversion factor of the system, i.e., the ratio of radiation input to light output, can also be measured a new imaging system and stored for later use in determining the operation of the same system when the image has deteriorated.

As will be apparent, the image evaluation apparatus 50 is useful in evaluating the system by providing a means for aligning the image intensifier image and the image optics to achieve a desired image quality. Furthermore, by providing a means of obtaining measurements of a satisfactory operating system, the system can later be quantitatively evaluated to determine whether problems exist when image quality has deteriorated. By simply measuring selected quantities and comparing those quantities with values representative of proper operation, it can be determined whether the image tube 40, the optical system 46 or the image gate 48 is defective. Still further, by utilizing the image evaluation apparatus 50 as a light source for generating an image having a predetermined quality and light intensity, the operation of camera systems connected to the imaging system 12 can also be evaluated and aligned.

It will be appreciated that what has been described in a preferred embodiment is a method and apparatus for in situ evaluation of an x-ray imaging system incorporating an electronic image apparatus for recording and presentation of x-ray images. While the invention has been described with reference to a preferred embodiment, certain modifications and changes will readily occur to those skilled in the art. Accordingly, the appended claims are intended to cover all such modifications or changes as thought within the spirit and scope of the invention.

We claim:

1. In an x-ray imaging system of the type including an x-ray source, an image intensifier tube for converting received x-ray radiation to optical images to be recorded photographically and/or electronically apparatus for in situ evaluation of the image intensifier tube performance comprising:
    a cylindrical housing having first and second ends;
    a lens mounted in said first end of said housing, said lens having a focal point at infinity;
    means for mounting said first end to the imaging system in position for receiving light from the image tube;
    a removable light diffuser mounted in said second end of said housing, said lens and said diffuser being arranged to be positioned exactly in the focal plane of said lens and displaying on said diffuser an image having a light intensity distribution proportional to the light intensity of the image produced by the image intensifier tube; and
    light intensity measuring means for evaluating the light intensity distribution on said diffuser for determining the light intensity produced by the image intensifier tube.

2. The apparatus of claim 1 and including a predetermined pattern formed in said diffuser light, said pattern including at least one circular sizing ring defining an ideal image size for the intensifier tube.

3. The apparatus of claim 1 wherein said mounting means includes a substantially flat plate adapted for mating to a camera attachment position on the imaging system, said housing being fixed to said mounting plate such that a longitudinal axis of said housing is normal to the plane of a mounting surface of said mounting plate.

4. The apparatus of claim 1 wherein said second end of said housing includes an internal enlarged bore defining an internal mounting shelf for supporting said light diffuser in a plane normal to said axis of said housing.

5. The apparatus of claim 4 and including a retaining ring dimension for fitting into said enlarged bore for holding said light diffuser against said internal mounting shelf.

6. The apparatus of claim 5 wherein said retaining ring includes a groove formed circumferentially about an outer surface, said housing including threaded apertures adjacent said second end for receiving retaining screws adapted for penetrating into said groove for maintaining said retaining ring in said housing.

7. The apparatus of claim 5 and including a light impervious plate dimensioned for fitting into said retaining ring over said light diffuser, said light impervious plate having a plurality of apertures at predetermined locations for defining locations for light intensity measurements.

8. A method for in situ evaluation of an x-ray imaging system of the type including an image intensifier tube for converting x-ray radiation into an optical image, and a lens system for projecting the optical image to at least one image presentation apparatus, said method comprising the steps of:

removing the at least one image presentation apparatus from the imaging system;

positioning an image evaluation apparatus in the location formerly occupied by the image presentation apparatus, the evaluation apparatus including a lens arrangement for focusing light from the optical image onto a light diffuser;

operating the imaging system for generating an optical image; and adjusting selected grid voltages of the image intensifier tube until the optical image viewed on the light diffuser is correctly sized.

9. The method of claim 8 and including the further step of adjusting selected grid voltages on the image intensifier tube until the optical image is focused on the light diffuser.

10. The method of claim 9 and including the further steps of:

adjusting the x-ray radiation to a predetermined value;

positioning a light impervious cover plate over the light diffuser, the cover plate having a plurality of apertures at predetermined locations; and determining the image intensity at each of the predetermined locations for establishing uniformity of image intensity.

* * * * *